United States Patent [19]

Schleppnik

[11] Patent Number: 4,622,221
[45] Date of Patent: Nov. 11, 1986

[54] METHOD, COMPOSITIONS AND COMPOUNDS, USEFUL IN ROOM FRESHENERS EMPLOYING CYCLOHEXYL ALCOHOL AND ESTER DERIVATIVES

[75] Inventor: Alfred A. Schleppnik, St. Louis, Mo.

[73] Assignee: Bush Boake Allen Inc., Montvale, N.J.

[21] Appl. No.: 581,772

[22] Filed: Feb. 21, 1984

Related U.S. Application Data

[60] Continuation-in-part of Ser. No. 352,642, Feb. 26, 1982, abandoned, and Ser. No. 352,643, Feb. 26, 1982, abandoned, and a continuation of Ser. No. 102,383, Nov. 12, 1979, abandoned, which is a continuation of Ser. No. 936,296, Aug. 23, 1978, abandoned, which is a division of Ser. No. 640,614, Dec. 15, 1975, abandoned, said Ser. No. 352,642, is a continuation of Ser. No. 127,658, Mar. 6, 1980, abandoned, which is a continuation of Ser. No. 761,750, Jan. 24, 1977, abandoned, which is a division of Ser. No. 628,855, Nov. 5, 1975, abandoned, said Ser. No. 127,658, is a continuation of Ser. No. 628,855, Nov. 5, 1975.

[51] Int. Cl.[4] .......................... A61L 9/01; A61L 9/04
[52] U.S. Cl. ......................................... 424/76; 424/45
[58] Field of Search .................................. 424/76, 45

[56] References Cited

PUBLICATIONS

Arctander; Perfume and Flavor Chemicals I(1969), # 36–38, 285, 286, 432–445, 579, 580, 775–785, 791–804, 813–817, 940–942, 970, 971, 1197–1206 and 2177–2181.
Arctander; Perfume and Flavor Chemicals II(1969), # 1845, 1846, 1970–1981, 2176, 2689, 2690, 2724, 2725, 2883, 2895–2998.
Mushenko et al., C.A., vol. 66 (1967), 65158q.
Buchanan, C.A., vol. 71(1969), 76034a.
Zeinalov et al., C.A., vol. 63 (1965), 11378–11379.

*Primary Examiner*—Allen J. Robinson
*Attorney, Agent, or Firm*—Kane, Dalsimer, Kane, Sullivan and Kurucz

[57] ABSTRACT

Compounds of the formula

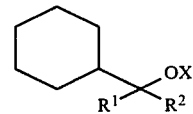

wherein $R^1$ is $C_{1-5}$ alkyl, $R^2$ is selected from hydrogen and $C_{1-5}$ alkyl, X is selected from hydrogen and $-COR^3$ wherein $R^3$ is selected from hydrogen and $C_{1-6}$ alkyl are useful in room freshners and other compositions for counteracting malodors in air, wherein the malodors are caused by one or more compounds selected from lower carboxylic acids, thiols, thiophenols, phenols, lower amines, phosphines and arsines. The defined compounds impart little or no fragrance to such compositions but the compositions may include additional fragrances. Particularly valuable and novel compounds are those wherein $R^1$ is methyl, $R^2$ is selected from hydrogen and methyl and X is $-COR^3$ wherein $R^3$ is $C_{2-6}$ alkyl.

10 Claims, No Drawings

METHOD, COMPOSITIONS AND COMPOUNDS, USEFUL IN ROOM FRESHENERS EMPLOYING CYCLOHEXYL ALCOHOL AND ESTER DERIVATIVES

CROSS-REFERENCE TO RELATED APPLICATIONS

This application is a continuation-in-part of copending application Ser. No. 352,642 filed Feb. 26, 1982, now abandoned, and of copending application Ser. No. 352,643, filed Feb. 26, 1982 and now also abandoned; a continuation of application of Ser. No. 102,383 filed on Nov. 12, 1979, now abandoned, and which in turn was a continuation of application Ser. No. 936,296 filed on Aug. 23, 1978, now abandoned, which in turn was a division of application Ser. No. 650,614 filed on Dec. 15, 1975 and now abandoned. The application Ser. No. 352,642 described above was a continuation of application Ser. No. 127,658 filed on Mar. 6, 1980, now abandoned, which in turn was a continuation of application Ser. No. 761,750 filed on Jan. 24, 1977, now abandoned and which was a division of application Ser. No. 628,855 filed Nov. 5, 1975, now abandoned. The application Ser. No. 127,658, filed Mar. 6, 1980, now abandoned, was a continuation of Ser. No. 628,855, filed Nov. 5, 1975.

A wide variety of room freshener (alternatively known as room deodorant) compositions have been developed for the purpose of freshening air that is contaminated with an odour that is offensive to the human sense of smell. Particularly unpleasant odours are caused by compounds which have a pronounced tendency to donate or accept protons and in particular compounds which are lower carboxylic acids, thiols, thiophenols, phenols, lower amines, phosphines or arsines. Compounds of these classes that have unpleasant odours are referred to herein as malodor compounds.

Conventional room fresheners include a plurality of fragrance materials that, together, combine to give a pleasant perfume that masks the malodor. The masking effect of the room fresheners is generally achieved by one of two mechanisms. In one mechanism, the masking fragrance, or part of it, blends with the malodor so as to provide a different and more desirable aroma. In the other mechanism the masking fragrance is utilised in sufficiently large quantities that it simply swamps the malodor.

Unfortunately both types of room freshening effect suffer from serious disadvantages. Generally neither completely eliminates the perception of malodor and so there is inevitably a tendency to apply ever increasing amounts of room freshener in an attempt, that is generally unsuccessful, of completely eliminating the perception of maldor. Secondly, the masking effect in both mechanisms is an additive effect and so the total odour level in the allegedly freshened air is increased by the application of the room freshener. Even though the fragrances used in the room freshener may, in small quantities, be very pleasant the total odour level in the air at concentrations sufficient to achieve moderate masking of the malodor may itself be offensive.

The skilled perfumer therefore knows that he must incorporate in the room freshener compositions only those perfuming ingredients that will contribute usefully to the odour of the composition and to the masking of the malodor, either by a smothering effect or by a blending effect. He therefore knows that he must not incorporate into the room freshener compositions fragrance compounds which do not contribute usefully to this effect or, worse, he must not incorporate fragrance compounds which themselves have an undesirable fragrance.

Certain alkyl substituted cyclohexyl compounds are known to have interesting perfumery properties. For instance certain alkyl substituted cyclohexyl alcohols are disclosed in U.S. Pat. No. 3,514,489 and British Pat. No. 1,476,720 and substituted cyclohexyl aliphatic esters having perfumery properties are disclosed in British Pat. No. 1,254,198 and U.S. Pat. No. 3,847,975.

Various unsubstituted cyclohexyl alcohols and a few unsubstituted cyclohexyl esters are known but none of these compounds have been disclosed as having useful perfumery properties.

Disclosures of unsubstituted cyclohexyl alcohols include the following:

cyclohexylmethanol by German Pat. No. 878,394; 1-cyclohexyl-1-ethanol by P. Sabatier, et al., Comptes rend. 139, 343 (1904); 1-cyclohexyl-1-propanol by D. Nightingale, et al., J. Org. Chem. 14, 1089 (1979); 1-cyclohexyl-2-methyl-1-propanol in E. P. Burrows, et al., JACS 82, 880 (1960); 1-cyclohexyl-1-butanol by D. Nightingale, et al. J. Org. Chem. 14, 1089 (1949); 1-cyclohexyl-1-pentanol by E. P. Burrows, et al., JACS 82, 880 (1960) and 2-cyclohexyl-2-propanol by G. S. Skinner, et al., JACS 76, 3200 (1954).

Various unsubstituted cyclohexyl methyl esters are disclosed by Zeinalov in Chemical Abstracts Vol. 63, 11378R. Unsubstituted cyclohexyl ethyl formate is disclosed in Japanese Patent Publication No. 68-29747. Certain unsubstituted cyclohexyl alkyl acetates are disclosed by Muschenko in Chemical Abstracts 1967 Vol. 66, 65158Q, Buchanan Chemical Abstracts Vol. 71 76034A, Overberger in JACS Vol. 81, 1959 4697 and Kugatova in Zhur Obs. Khim. 1961 31 604 but none of these disclosures suggest perfumery properties of these compounds.

Upon reviewing the fragrance properties of a variety of unsubstituted cyclohexyl alcohols and esters, none were found to be of potential value for contributing to the chosen odour of a room freshener by the conventional masking or blending mechanisms. In particular, none had an odour that was such as to suggest to the perfumer that they should be incorporated in room fresheners or other perfumed compositions. The alcohols generally had an unpleasant odour (whereas the alkyl substituted cyclohexyl alcohols often had a pleasant and useful odour) and were thus clearly contraindicated. Although some alkyl substituted cyclohexyl esters had a pleasant odour the unsubstituted cyclohexyl esters generally had an unpleasant odour or, at best, an odour that was tolerable but which did not suggest to the perfumer that the compound would be useful in a perfumery composition. Again therefore the esters were contraindicated.

We have now surprisingly found that despite the unpleasant or uninteresting fragrance properties of certain unsubstituted cyclohexyl alcohols and esters these compounds are in fact very useful components of room freshener and other perfumery compositions for use against the defined malodors.

The compounds to which the invention relates are compounds of the formula

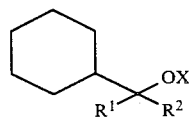

wherein $R^1$ is $C_{1-5}$ alkyl, $R^2$ is selected from hydrogen and $C_{1-5}$ alkyl and X is hydrogen or —$COR^3$ wherein $R^3$ is selected from hydrogen and $C_{1-6}$ alkyl.

It is particularly surprising that the alcohols, that is to say the compounds wherein X is hydrogen, are useful for such purposes since their odours are generally unpleasant and clearly contraindicate their use in perfumery compositions. Preferred alcohols are those in which $R^1$ is Methyl, and $R^2$ is hydrogen, or methyl, the compound in which $R^2$ is hydrogen and $R^1$ is methyl being particularly preferred.

It is particularly surprising that the defined esters, that is to say the compounds in which X represents —$COR^3$, are useful for the described purposes since their odours are either unpleasant or, at best, uninteresting but they do, in room freshener compositions used against the defined malodors, give extremely valuable properties to the compositions. The preferred esters are those wherein $R^3$ is selected from $C_{1-3}$ alkyl and wherein $R^1$ is Methyl, and $R^2$ is hydrogen or methyl. Particularly good and surprising results are obtained from those compounds wherein $R^1$ is hydrogen, $R^2$ is methyl and $R^3$ is methyl, n-propyl or isopropyl, most preferably n-propyl. The preferred compound for use in the invention is the ester wherein $R^3$ is n-propyl, namely cyclohexyl-1-ethyl-n-butyrate.

The esters wherein $R^3$ is an alkyl group containing 2 to 6 carbon atoms are new compounds, the compounds wherein $R^3$ is isopropyl or, particularly, n-propyl being especially preferred novel compounds.

It has been found that the defined esters and alcohols have a useful effect against malodors entirely different from the masking effect obtained by conventional room fresheners that blend or swamp the offensive malodor. The effect of the defined compounds is not an additive effect of the type that is conventionally present and which results in the perceived odour level generally increasing significantly at the effective concentration of the composition. Instead the effect is what I term a counteractant effect, that is to say the perceived total odour level is reduced at the effective concentration of the composition and the perceived odour level of the malodor is substantially entirely eliminated at this effective concentration. Thus these compounds have two great advantages over conventional room freshener compositions. Firstly they can result in the total or substantial elimination of the perceived odour level of the defined malodor, and so the user is not encouraged to dose the air with ever increasing amounts of the composition in a struggle to try to swamp the malodor to such an extent that its perceived odour level is very low. Secondly, because the malodor effect is eliminated whilst reducing the total odour level the use of the compounds does not result in the total perceived odour level increasing, and instead the total perceived odour level after administration of the compositions of the invention is normally substantially below the total perceived odour level before administration. This is despite the fact that preferred compositions of the invention include not only the malodor but also a plurality of conventional fragrance ingredients. These ingredients impart to the air the desired perfumed effect and also will mask any undesired odours of a chemical type different from the defined malodors that are treated in the invention.

It seems that the compounds defined in the invention have the effect of eliminating the perception by the observer of malodor without eliminating the perception of other odours by the observer. Without being bound by theory it seems possible that the defined compounds block the observers receptor sites that record the presence of the malodor without blocking the observers receptor sites that record the presence of other odours.

As an example of this mechnism one can compare the effect on an atmosphere containing 10 parts per billion methyl mercaptan (as the malodor) of varying levels ranging from 1 part per trillion to 100 parts per billion of a conventional lemon fragrance with the effect of a similar lemon fragrance containing one of the defined compounds, for instance cyclohexyl-1-ethyl-n-butyrate.

With the conventional fragrance, first an initial decline both in perceived overall odour intensity and perceived malodor intensity is observed, up to a concentration of around 100 ppt fragrance. At this point the perceived overall odour intensity goes to a minimum and starts to rise again with increasing fragrance concentrations whilst the perceived malodor intensity almost plateaus off. In the fragrance range 220 ppt to 20 ppb there is a significant increase in perceived overall odour intensity and only a slight decrease in the perceived malodor intensity and this seems to be the region of true masking, the overall odour consisting of a certain ratio of malodor to fragrance. Further increase in fragrance concentration only very slightly reduces the perceived malodor intensity but leads to a steady increase in perceived total odour intensity until it becomes over powering. Even at 100 ppb fragrance, when the total intensity is very high, there is still significant perception of malodor.

When the corresponding observations are conducted using a fragrance composition containing the defined counteractant, a very different effect is observed. First there is a rapid decline both of the perceived total intensity and of the perceived malodor intensity. Substantially total elimination of any perception of malodor is achieved at a relatively low concentration of total fragrance composition, typically around 60 ppt. At this point the perception of overall odour intensity goes to a minimum and the addition of further fragrance to the air merely results in a rapid increase of the total perceived odour intensity, the character of the odour suggesting that it is due solely to the applied fragrance and is very little influenced by the malodor that was present initially and there is substantially no perception of the malodor.

The defined compounds are conveniently referred to as malodor counteractants and they are applied to the air containing the malodor in an amount that results in effective counteraction of the malodor. The amount will depend on variables such as the medium in which the compound is used and the temperature, humidity and air circulation. Generally the amount is within the range 0.01 to 1 mg per cubic meter of air.

The compounds may be applied to the air either directly, for instance in a conventional room freshener (or deodorant) composition such as an aerosol or other spray, a wick or other liquid system, or a solid, for instance a wax base as in pomanders and plastics, powders as in sachets or dry sprays or gels, as in solid gel sticks, or they may be applied to the air indirectly. For instance they may be included in clothes deodorants as applied by washing machine applications such as in detergents, powders, liquids, whiteners or fabric softeners or by other applications such as closet blocks, closet aerosol sprays, or clothes storage areas or in dry cleaning to overcome residual solvent notes on clothes; in bathroom accessories such as paper towels, bathroom tissues, sanitary napkins, towellets, disposable wash cloths, disposable diapers, and diaper pail deodorants; in cleansers such as disinfectants and toilet bowl cleaners; in cosmetic products such as antiperspirant and underarm deodorants, general body deodorants in the form of powders, aerosols, liquids or solid, or hair care products such as hair sprays, conditioners, rinses, hair colours and dyes, permanent waves, depilatories, hair straighteners, hair groom applications such as pomade, creams and lotions, medicated hair care products containing such ingredients as selenium sulphide, coal tar or salicylates, or shampoos, or foot care products such as foot powders, liquids or colognes, after shaves and body lotions, or soaps and synthetic detergents such as bars, liquids, foams or powders; in odour control such as during manufacturing processes, such as in the textile finishing industry and the printing industry (inks and paper); in effluent control such as in processes involved in pulping, stock yard and meat processings, sewage treatment, or garbage disposal, or in product odour control as in textile finished goods, rubber finished goods or car fresheners; in agricultural and pet care products such as dog and hen house effluents and domestic animal and pet care products such as deodorants, shampoo or cleaning agents, or animal litter material and in large scale closed air systems such as auditoria, and subways and transport systems.

Thus it will be seen that the composition of the invention is usually one in which the malodor counteractant is present together with a carrier by means of which or from which the malodor counteractant can be introduced into the atmosphere containing the malodor. For example the carrier can be an aerosol propellant such as a chlorofluoro-methane, or a solid such as a wax, plastics material, rubber, inert powder or gel. In a wick-type air freshener, the carrier is a substantially odourless liquid of low volatility. In several applications, a composition of the invention contains a surface active agent or a disinfectant, while in others, the malodor counteractant is present on a fibrous substrate. In many compositions of the invention there is also present a fragrance component which imparts a fragrance to the composition, and often includes a plurality, for example at least three, ingredients, for instance lavandin abrialis oil, amyl salicylate, geraniol, isopulegol, musk xylol, terpinyl acetate or ylang ylang oil. The amount of the fragrance component present in a composition of the invention containing such a component is generally at least equal to that of the malodor counteractant, and preferably the amount of the former exceeds that of the latter such that the weight ratio of fragrance component to malodor counteractant is within the range 1.1:1 to 20:1, and more specifically within the range 2:1 to 15:1. Typically the concentration of malodor counteractant in the composition is in the range 0.02 to 0.2% by weight of the total weight of the composition.

The malodor counteractant compounds which are alcohols can be made by conventional techniques, including those used previously for making the compounds. For instance benzene may be reacted with an appropriate acid chloride to form, for instance, acetophenone and this may be catalytically reduced to form the desired product. Alternatively benzoic acid may be catalytically reduced using rhodium catalyst and the resultant cyclohexyl carboxylic acid reduced using copper chromite catalyst to form the desired alcohol. Cyclohexyl carboxylic esters can be subjected to a Grignard reaction to form the desired alcohol. Particular examples are given in British Patent Specification No. 1,545,562. The malodor counteractants that are esters can be made by esterification of the corresponding cyclohexyl alkyl alcohol. Methods for the known compounds appear in the literature and are also described in British Patent Specification No. 1,545,561.

Odours of various alkyl substituted cyclohexyl alkanols are as follows:

cistrans-4-tert.butyl cyclohexyl methanol, green fresh steamy floral jasmine cis/trans-1-(4-tert.butyl cyclohexyl)-1-ethanol, sharp floral musky cis/trans-1-(4-ethyl cyclohexyl)-1-ethanol, floral woody fresh rose.

cis/trans-1-(methylcyclohexyl)-1-ethanol sour citrus lime camphor cis/trans-1-(4-methylcyclohexyl)-1-ethanol, animal castoreum leather cis.trans-4-tert.butyl cyclohexyl methanol, lacking a sandalwood odour cis/trans-1-(4-tert.butylcyclohexyl)-2-propanol (dihydroterpineol), lilac but more pine like/woody than alphaterpineol cis trans 2-(4-methylcyclohexenyl)-2-propanol (alpha terpineol), lilac 1-cis(4-isopropenylcyclohexyl)-methanol, flowery (U.S. Pat. No. 3993604)

1-trans(4-isopropenyl cyclohexyl)-methanol, chemical (U.S. Pat. No. 3993604)

1-[3,3 gem dimethylcyclohexyl]ethanol, floral woody or sweet mint camphor.

From this it will be seen that many have potential value in fragrance compositions.

According to Arctander in Perfume and Flower Chemicals 1969 page 796 cyclohexylmethanol has a musty camphoraceous slightly minty odour, remotely reminiscent of part of the Patchouli odour-picture; 2 cyclohexyl propan-1-ol, very mild balsamic floral odour (Arctander Page 803); 3 cyclohexyl propan-1-ol, very mild sweet balsamic odour but rather flat (Arctander page 804); 2 cyclohexylethan-1-ol, dry camphoraceous odour, little resemblance to rose and patchouli, No floral odour. (Arctander page 791).

The odours of unsubstituted cyclohexyl alkanols of the invention are as follows:

cyclohexyl-1-ethanol, very sharp chemical camphoraceous cyclohexyl-1-propanol, very chemical cyclohexyl-1-butanol, dirty minty chemical 2 cyclohexyl-2-propanol sharp and dirty chemical, hint of lime.

These odours are objectionable to a perfumer because of their chemical odour.

Odours of various substituted cyclohexyl alkyl esters are as follows:

4-isopropylcyclohexylmethyl acetate, fragrant, generally flowery

[4-isopropyl cyclohexyl]-1-ethanol acetate-animal odour [2,2-dimethyl-6-methyl cyclohexyl methanol acetate-mild oily rosy fruity somewhat green 2-(4'-methyl cyclohexyl)-2-propanol acetate-fresh, piney, citrusey, minty, camphoraceous herbaceous 1-(3,3-dimethylcyclohexyl)-1-ethanol acetate-sweet woody, floral 1-(3-methylcyclohexyl)-1-ethyl acetate-fresh, clean, minty, woody.

4-methylcyclohexyl-1-ethanol acetate-floral green, powerful (2,4-dimethylcyclohexyl)-1-ethanol acetate-Powerful green, fruity, but overall sweet 2-(4'-methylcyclohexenyl)-2-propanol acetate-Mild herbaceous sweet spicy bergamot, lavender 2-cyclohexylethanol acetate-Powerful, sweet, fruity nondescript.

(Arctander page 1202). Accordingly it is apparent that some of these are potentially useful in fragrances.

The odours of the 1-cyclohexylalkyl esters used in the invention are as follows (referring to the structural formula shown above):

| Compound | $R^2$ | $R^1$ | $R^3CO$ | Odour |
|---|---|---|---|---|
| A | H | Me | MeCO | Fruity floral woody solvent like chemical |
| B | H | Me | EtCO | Fatty dirty, oily |
| C | H | Me | iPrCO | Fruity with floral overtones |
| D | H | Me | PrCO | Fatty metallic with fruity floral overtones |
| E | Me | Me | MeCO | Chemical solvent like |
| F | Me | Me | EtCO | Chemical camphoraceous |
| G | Me | Me | iPrCO | Floral citrus muguet |
| H | Me | Me | PrCO | Chemical fruity |
| I | H | Et | MeCO | Faint chemical minty. |

From this it is apparent that none would be attractive to the perfumer for use in fragrances and, in particular, compounds A, B, D, E, F, H and I would definitely be avoided by the perfumer because of the undesirable chemical note that they would inevitably introduce into the fragrance. Even compounds C and G are uninteresting to the perfumer because they do not have that special quality that a compound must have if it is to be of interest to the perfumer for incorporation in a fragrance.

The invention is illustrated in the following examples.

EXAMPLE 1

1-CYCLOHEXYL-1-ETHYL FORMATE

A mixture of 12.8 g. (0.1 moles) 1-cyclohexyl-1-ethanol and 13.8 g. (0.3 moles) formic acid was refluxed for two hours and then cooled to room temperature. It was poured in 200 ml. cold water, the organic material extracted in ether and the ether extract washed thoroughly with water, sodium bicarbonate, water and brine and dried over molecular sieves. 15.4 g. crude product of 97.9% purity was recovered—major impurity is residual solvent. The crude product was distilled through a short Vigreux-column. The product is a mobile, colorless liquid, b.p. 94° C./16 mm., $n_D^{25}=1.4437$. Yield 13.6 g.=87.1%, purity 99.2% (by GLC) of 1-cyclohexyl-1-ethyl formate.

EXAMPLE 2

1-CYCLOHEXYL-1-ETHYL ACETATE

A mixture of 25.6 g. (0.2 moles) 1-cyclohexyl-1-ethanol and 22.0 g. acetic anhydride (0.22 moles) containing 100 mg. p-toluene sulfonic acid was warmed to 50° C. A strongly exothermic reaction occurred which was allowed to proceed freely. A maximum temperature of 123° C. was reached. After standing at room temperature the reaction mixture was diluted with the same volume of ether and poured into 300 ml. cold water. The organic layer was separated, thoroughly washed with water (4×50 ml.), sodium bicarbonate solution, water again and finally brine. The solvent was evaporated on a rotary evaporator to give 33.5 g. of crude product, purity 98.76% by GLC. Distillation through a short Vigreux-column afforded 30.8 g. of pure product, b.p. 85° C./10 mm., $n_D^{24}=1.4445$, colorless liquid of fruity-floral-woody odor with a touch of an animal note. NMR analysis confirmed the product as 1-cyclohexyl-1-ethyl acetate.

EXAMPLE 3

1-CYCLOHEXYL-1-ETHYL PROPIONATE

To a mixture of 12.8 g. (0.1 moles) 1-cyclohexyl-1-ethanol and 14.3 g. (0.11 moles) propionic anhydride was added 100 mg. p-toluene sulfonic acid and the mixture left at room temperature for 18 hours. Then 0.2 ml. water was added and the mixture left one more hour at room temperature and then poured in 200 ml. cold water. The organic layer was separated, the aqueous layer extracted once with ether and the combined organic material washed with water, sodium bicarbonate, water and finally brine. After drying over molecular sieves afforded 18.6 g. of crude material, $n_D^{23}=1.4442$ which was practically pure. Distillation through a short Vigreux-column afforded the product, b.p. 98.5° C./10 mm., $n_D^{24}=1.4446$, yield 15.5 g.=84.1%. Purity 99.7% by GLC of 1-cyclohexyl-1-ethyl propionate having a fatty, dirty and oily odor.

EXAMPLE 4

1-CYCLOHEXYL-1-ETHYL ISOBUTYRATE

A solution of 25.6 g. (0.2 moles) 1-cyclohexyl-1-ethanol and 19.4 g. (0.22 moles) isobutyric acid in 100 ml. benzene, containing 2 g. p-toluene sulfonic acid, was heated to gentle reflux-water distilled at a reasonable rate. After refluxing overnight 3.6 ml. of water were collected. The mixture was extracted with excess cold saturated sodium bicarbonate solution, washed with water and brine and evaporated on a rotary evaporator to give 38.1 g. of a colorless fragrant liquid, $n_D^{25}=1.4435$. GLC=91.94% product and 6.91% low boilers. The product was purified by distillation through a Holtzmann-column. After a small forerun (discarded) the product was obtained as a colorless fragrant liquid, b.p. 56° C./0.3 mm., $n_D^{25}=1.4420$, yield 33.5 g. (83.2%). NMR analysis confirmed the product as 1-cyclohexyl-1-ethyl isobutyrate.

EXAMPLE 5

1-CYCLOHEXYL-1-ETHYL n-BUTYRATE

To a mixture of 12.8 g. (0.1 moles) 1-cyclohexyl-1-ethanol and 9.7 g. (0.11 moles, 10% excess) n-butyric acid in 50 ml. benzene was added 1 g. p-toluene sulfonic acid and with stirring refluxed gently overnight. 1.8 ml. (calculated amount) water were collected in a trap. The benzene solution was allowed to cool to room temperature, then washed with sodium bicarbonate solution, water and brine, and evaporated on a rotary evaporator to give 18.3 g. of crude ester, $n_D^{24}=1.4462$, purity 95.9%. Distillation through a short Vigreux-column gave the pure product, b.p. 97.5° C./4 mm., $n_D^{25}=1.4456$, yield 15.4 g. (77.7%), purity by GLC 99.7% of 1-cyclohexyl-1-ethyl n-butyrate which is a colorless, mobile fragrant liquid.

EXAMPLE 6
1-CYCLOHEXYL-1-PROPYL ACETATE

A mixture of 1.42 g. 1-cyclohexyl-1-propanol and 11.2 g. acetic anhydride containing 100 mg. p-toluene sulfonic acid was left at room temperature for 24 hours. It was then poured in excess (200 ml.) water, the organic material extracted with ether and the ether layer washed thoroughly with water and sodium bicarbonate solution and brine and dried over molecular sieves. 15.8 g. of crude product, $n_D^{25}=1.4456$ was recovered. It was distilled through a short Vigreux-column to give two fractions

| | | |
|---|---|---|
| b.p. 69° C./2 mm., | $n_D^{25} = 1.4456$ | 1.6 g. (Fraction 1) |
| b.p. 69° C./2 mm., | $n_D^{25} = 1.4456$ | 13.5 g. (Fraction 2) |

Fraction 2 was 99.6% pure, by GLC, 1-cyclohexyl-1-propyl acetate.

EXAMPLE 7
1-CYCLOHEXYL-1-PROPYL n-BUTYRATE

A solution of 14.2 g. (0.1 moles) 1-cyclohexyl-1-propanol and 9.7 g. n-butyric acid (10% excess) in 50 ml. benzene containing 0.25 ml. concentrated sulfuric acid was heated to reflux and water collected in a Dean-Stark trap. 13.1 g. (61.7%) of crude product, $n_D^{23}=1.4508$ were recovered. Two low boiling minor peaks suggest that considerable dehydration had occurred. Distillation of the crude product through a short Vigreux-column afforded two fractions

| | | |
|---|---|---|
| b.p. 23–76° C./0.7 mm., | $n_D^{23} = 1.4518$ | 3.8 g. (Fraction 1) |
| b.p. 72° C./0.4 mm., | $n_D^{23} = 1.4470$ | 8.3 g. (Fraction 2) |

Fractions 2, 1-cyclohexyl-1-propyl n-butyrate, a colorless mobile liquid, had a weak fruity, prune-like odor.

EXAMPLE 8
1-CYCLOHEXYL-2-METHYL-1-PROPYL ACETATE

To a mixture of 15.6 g. (0.1 moles) 1-cyclohexyl-2-methyl-1-propanol and 11.2 g. (0.11 moles) acetic acid was added 100 mg. p-toluene sulfonic acid and the mixture left at room temperature overnight. Then 1 g. sodium acetate and 1 ml. water was added, the mixture stirred for one hour and poured into 150 ml. water. The organic layer was separated, the aqueous layer extracted with 2×50 ml. ether and the combined extracts and organic layer washed thoroughly with water, sodium bicarbonate solution, water and brine. After drying over molecular sieves overnight 17.4 g. of crude product, $n_D^{23}=1.4482$, was recovered which was practically pure. Distillation through a Vigreux-column gave the pure product, b.p. 79° C./2.9 mm., $n_D^{25}=1.4477$ which was 1-cyclohexyl-2-methyl-1-propyl acetate.

EXAMPLE 9
2-CYCLOHEXYL-2-PROPYL ACETATE 21.3 g. recovered 2-cyclohexyl-2-propanol were dissolved in 20.0 g. acetic anhydride and 500 mg. 85% phosphoric acid added. Monitoring by IR showed that all of the alcohol had reacted overnight. 20 ml. water and 1.0 g. anhydrous sodium acetate were added and the mixture stirred at room temperature for one hour to hydrolyze excess acetic anhydride. Then it was poured into cold water, extracted with ether and the ether solution backwashed with water, sodium bicarbonate solution and brine and evaporated on a rotary evaporator to give 19.3 g. of crude material which analyzed by GLC to 23% mixture of two hydrocarbons and 76% of 2-cyclohexyl-2-propyl acetate. It was distilled through a Holtzmann-column:

| | | |
|---|---|---|
| b.p. 27° C./0.5 mm., | $n_D^{25} = 1.4600$ | 2.0 g. (Fraction 1) |
| b.p. 42° C./0.1 mm., | $n_D^{25} = 1.4505$ | 14.3 g. (Fraction 2) |

Fraction 2 was 99% of the desired product by GLC. NMR analysis confirmed its structure.

EXAMPLE 10
2-CYCLOHEXYL-2-PROPYL PRIPIONATE

A mixture of 28.4 g. 2-cyclohexyl-2-propanol (0.2 moles) 39.0 g. propionic anhydride (0.3 moles) and 22.3 g. (0.22 moles) triethyl amine were heated with stirring to 120° C. and the progress of reaction monitored by GLC. After 7 hours almost all of the alcohol had been consumed and the reaction mixture was left at room temperature overnight. It than was poured into excess water and the organic layer separated. The aqueous layer was extracted with benzene, the benzene extract combined with the organic layer and thoroughly washed with water, 3% hydrochloric acid, water, sodium bicarbonate solution, water and finally with brine. The solvent was removed on a rotary evaporator at 30 mm. pressure and 50° C. bath temperature. 38.6 g. of crude product, $n_D^{25}=1.4475$, were obtained and distilled through a short Vigreux-column:

| | | |
|---|---|---|
| b.p. up to 69° C./0.7 mm., | $n_D^{25} = 1.4210$ | 1.9 g. (Fraction 1) |
| b.p. up to 62° C./0.35 mm., | $n_D^{25} = 1.4504$ | 32.2 g. (Fraction 2) |

The product is 96.8% pure 2-cyclohexyl-2-propyl propionate by GLC, impurity is unreacted 2-cyclohexyl-2-propanol (GLC analysis). The product is a colorless, mobile liquid with a chemical, camphoraceous odor.

EXAMPLE 11
2-CYCLOHEXYL-2-PROPYL ISOBUTYRATE

A mixture of 28.4 g. (0.2 moles) 2-cyclohexyl-2-propanol 40.0 g. (0.25 moles) isobutyric anhydride and 22.3 g. (0.22 moles) triethyl amine was heated to reflux overnight and the product was recovered as described in Example 33 to give 42.7 g. of a crude product, $n_D^{25}=1.4442$. Distillation through a short Vigreux-column afforded:

| | | |
|---|---|---|
| b.p. 43° C./0.5–60° C./0.3 mm., | $n_D^{24} = 1.4278$, | 8.5 g. (Fraction 1) |
| b.p. 70° C./0.7 mm., | $n_D^{24} = 1.4475$, | 33.0 g. (Fraction 2) |

Fraction 1 contained unreacted and unhydrolyzed isobutyric anhydride. The product was 98.7% (GLC analysis) pure 2-cyclohexyl-2-propyl isobutyrate. The product was a colorless, mobile liquid with a floral, citrus, rose muguet odor.

EXAMPLE 12

2-CYCLOHEXYL-2-PROPYL n-BUTYRATE

To a solution of 28.4 g. (0.2 moles) 2-cyclohexyl-2-propanol and 24.0 g. (0.3 moles) pyridine in 100 ml. anhydrous ether, chilled in an ice-salt bath, was added with stirring a solution of 23.4 g. (0.22 moles) freshly redistilled butyryl chloride at such a rate as to keep the temperature around 0° C. The ice bath was removed after complete addition and stirring continued for two hours. Then the solid was dissolved in the minimum amount of water and the organic layer separated. It was washed with water, 3% hydrochloric acid, water, sodium bicarbonate solution, water again and finally with brine. After drying over molecular sieves overnight a crude product (42.0 g.) was recovered, $n_D{}^{25}=1.4603$. This product contained unreacted alcohol as a major impurity. Distillation through a short Vigreux-column afforded:

| b.p. up to 67° C./0.25 mm., | $n_D{}^{25} = 1.4548$ | 4.5 g. (Fraction 1) mostly low boilers |
|---|---|---|
| b.p. 67–71° C./0.2 mm., | $n_D{}^{25} = 1.4522$ | 27.2 g. (Fraction 2) mostly product |

Fraction 2 was redistilled:

| b.p. 48–60° C./0.1 mm., | $n_D{}^{25} = 1.4572$ | 5.3 g. (Fraction 2A) |
|---|---|---|
| b.p. 60° C./0.1 mm., | $n_D{}^{25} = 1.4514$ | 20.8 g. (Fraction 2B) |

Fraction 2B was analyzed by GLC to 99.9% purity 2-cyclohexyl-2-propyl n-butyrate. The product was a colorless, mobile liquid with a chemical, fruity odor.

EXAMPLE 13

The following malodor concentrate was prepared:

| Bathroom Malodor Concentrate | |
|---|---|
| Component | Parts by Wt. |
| skatole | 0.91 |
| β-thionaphthol | 0.91 |
| 95% aqueous solution of thioglycolic acid | 21.18 |
| n-caproic acid | 6.00 |
| p-cresyl isovalerate | 2.18 |
| N—methyl morpholine | 6.00 |
| dipropylene glycol | 62.82 |

Aerosol cans were prepared with the above malodor with the following concentrations:

| Bathroom Malodor Aerosol | |
|---|---|
| Component | Parts by Wt. |
| Bathroom Malodor Concentrate | 0.1 |
| dipropylene glycol | 4.9 |
| Propellant | |
| a. trichloromonofluoromethane | 47.5 |
| b. dichlorodifluoromethane | 47.5 |

A "Spice for Cologne" fragrance was selected for use in testing the malodor counteractant ability of the compounds tested. The "Spice for Cologne" fragrance contained the following ingredients:

| Ingredients | Parts by Wt. |
|---|---|
| Lavandin Abrialis Oil | 60 |
| Amyl Cinnamic Aldehyde | 20 |
| Amyl Salicylate | 150 |
| Benzyl Acetate | 30 |
| Linalool | 30 |
| Cedarwood Oil | 10 |
| Geraniol | 130 |
| Isopulegol | 60 |
| Methyl Anthranilate (10% by weight solution in dipropylene glycol) | 20 |
| Musk Xylol | 60 |
| Coumarin | 50 |
| Phenyl Ethyl Acetate | 30 |
| Terpinyl Acetate | 100 |
| Cinnamon Leaf Oil | 40 |
| Petitgrain Oil SA | 60 |
| Ylang ylang Oil | 130 |
| Phenyl Acetaldehyde Dimethyl Acetal | 15 |
| Cinnamic Alcohol | 5 |
| | 1000 |

Aerosol cans were prepared with the above fragrance composition with and without 1-cyclohexyl-1-ethyl n-butyrate being present as a malodor counteractant as follows:

| | % by Wt. |
|---|---|
| Without 1-cyclohexyl-1-ethyl n-butyrate | |
| "Spice for Cologne" fragrance | 0.5 |
| Propellant | |
| a. trichloromonofluoromethane | 49.75 |
| b. dichlorodifluoromethane | 49.75 |
| | 100.00 |
| With 1-cyclohexyl-1-ethyl n-butyrate | |
| "Spice for Cologne" fragrance | 0.45 |
| 1-cyclohexyl-1-ethyl n-butyrate | 0.05 |
| Propellant | |
| a. trichloromonofluoromethane | 49.75 |
| b. dichlorodifluoromethane | 49.75 |
| | 100.00 |

A test chamber having inside dimensions of 3.35×3.66×2.44 (meters) with a total volume of 29.9 cubic meters, having an access door and an exhaust fan was provided. The capacity of the exhaust fan was 14 cubic meters/min. In order to insure satisfactory evacuation the exhaust fan was operated for five minutes between tests and an olfactory check was made to determine if any residual odor could be detected prior to conducting the next test.

After the test chamber had been suitably evacuated the bathroom malodor was sprayed from the aerosol can for about five seconds. After a delay of from 10–15 seconds the fragrance composition aerosol was sprayed for about five seconds (five seconds being an average time such an aerosol would usually be used by a housewife). One minute thereafter a 2 member panel (consisting of 1 person skilled in perfumery and odor evaluation and 1 person general) entered the test chamber, performed an olfactory evaluation for detection of the malodor and recorded their observations. All tests were performed with neither member of the panel being aware of the identity of the material being tested.

Based on the flow rate through the valve utilized in the aerosol can the approximate amount of aerosol, containing the malodor concentrate, introduced into the test chamber is:

| Aerosol Containing Malodor Concentrate | Amount (mg./cu.meter) |
|---|---|
| Bathroom | 267 |

The amount of aerosol containing the fragrance compositions introduced into the test chamber is approximately 260 mg./cu.meter.

When the above described test procedure was carried out using the "Spice for Cologne" fragrance composition aerosol with 1-cyclohexyl-1-ethyl n-butyrate neither member of the panel could detect the presence of the malodor. This is a particularly surprising result because when the "Spice for Cologne" fragrance composition aerosol without 1-cyclohexyl-1-ethyl n-butyrate is tested both members of the panel detected the presence of the malodor. The panel commented that the malodor counteractant effect was outstanding and that there was produced a fresh air effect (FAE), real ozone effect, with a very nice and low residual odor from the compound tested.

EXAMPLE 14

An aerosol can was prepared with the following concentrations:

| Component | Parts by Wt. |
|---|---|
| 1-cyclohexyl-1-ethyl n-butyrate | 0.05 |
| Propellant | |
| a. trichloromonofluoromethane | 49.975 |
| b. dichlorodifluoromethane | 49.975 |

The aerosol was utilized in the above-described test procedure (aerosol—267 mg./cu. meter). Neither member of the panel could detect the presence of the malodor. However, 1-cyclohexyl-1-ethyl-n-butyrate is not particularly pleasing in its odour properties when used alone.

EXAMPLE 15

The exemplary compounds indicated in Table 1 were incorporated into "Spice for Cologne" fragrance composition aerosol cans according to the procedures of Example 36 and, using the test procedures of Example 36, they were tested for their ability to counteract the bathroom malodor. The results are shown in Table 1.

TABLE 1

| Compound | Activity* | Comments |
|---|---|---|
| 1 | U* | FAE, very clean and extremely light and fresh |
| 2 | V | No malodor, light residual with a spicy note |
| 3 | U | FAE, very clean, very nice and fresh, low residual |
| 4 | U | FAE, very clean, fresh and low residual |
| 6 | WV | No malodor, stronger residual odour |
| 7 | U* | FAE, almost no residual odour |
| 8 | VU | No malodor, weak FAE, residual background |
| 9 | VU | FAE, slower action but very clean, fresh and light residual |
| 10 | VU | Borderline excellent, FAE slow, no sharp impact, no malodor, clean acceptable residual |
| 11 | U | FAE, clean and nice residual |
| 12 | U | FAE, clean and nice residual |

TABLE 1-continued

| Compound | Activity* | Comments |
|---|---|---|
| | | of lower intensity |

*Ability of compound to counteract the malodor according to the following scale:
U* "Outstanding" - Fresh air-effect pronounced and producing extremely light or no residual odor at all.
U "Excellent" - Fresh air effect and light and pleasant residual background odor.
V "Very good" - No fresh air effect but total abatement of malodors, variable, but not high residual background odor.
W "Good" - Only traces of malodor, often of changed quality remain. Residual background odor acceptable to pleasant, not too strong.
X "Fair" - Original malodor clearly discernable but of low intensity. Residual background odor acceptable at best
Y "Poor" - Original malodor somewhat reduced in intensity, but dominates. Overall residual background odor unpleasant to unacceptable.
Z "No activity".
**FAE - fresh air effect.

EXAMPLE 16

The alcohols indicated in Table 2 were tested as in Example 15 and the results are shown in Table 2.

TABLE 2

| Compound | Activity[1] | Comments |
|---|---|---|
| 1-cyclohexyl-1-ethanol | U | Clean, fresh, very light residual |
| 1-cyclohexyl-1-propanol | U | Very light, clean residual |
| 1-cyclohexyl-2-methyl-1-propanol | VU | Clean, light, weak FAE** |
| 1-cyclohexyl-1-butanol | U | Clean, light, nice residual |
| 1-cyclohexyl-1-pentanol | WV | No malodor, but perfumery residual |
| 2-cyclohexyl-2-propanol | U* | Very clean and fresh sea breeze |

I claim:

1. A method of counteracting a malodor in the air caused by a compound selected from the group consisting of lower carboxylic acids, thiols, thiophenols, phenols, lower amines, phosphines and arsines which comprises introducing into the air an effective malodor counteracting amount of cyclohexyl-1-ethyl-n-butyrate whereby the perceived total odour intensity in the air is reduced and the perceived malodor intensity in the air is substantially eliminated.

2. A method according to claim 1 in which the cyclohexyl-1-ethyl-n-butyrate is introduced into the air together with a plurality of fragrance materials and the perceived total odour intensity in the air is reduced and the perceived malodor intensity is substantially eliminated.

3. A method of counteracting a malodor in the air caused by a compound selected from the group consisting of lower carboxylic acids, thiols, thiophenols, phenols, lower amines, phosphines and arsines which comprises introducing into the air an effective malodor counteracting amount of cyclohexyl-1-ethyl acetate whereby the received total odour intensity in the air is reduced and the perceived malodor intensity in the air is substantially eliminated.

4. A method according to claim 3 in which the cyclohexyl-1-ethyl acetate is introduced into the air together with a plurality of fragrance materials and the perceived total odour intensity in the air is reduced and the perceived malodor intensity is substantially eliminated.

5. A method of counteracting a malodor in the air caused by a compound selected from the group consisting of lower carboxylic acids, thiols, thiophenols, phenols, lower amines, phosphines and arsines which comprises; introducing into the air an effective malodor counteracting amount of a malodor counteractant selected from the compounds having the formula:

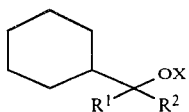

wherein $R^1$ is $C_{1-5}$ alkyl, $R^2$ is selected from the group consisting of hydrogen and $C_{1-5}$ alkyl and X is —$COR^3$ wherein $R^3$ is selected from the group consisting of hydrogen and $C_{1-6}$ alkyl, whereby the perceived total odor intensity in the air is reduced and the perceived malodor intensity is substantially eliminated.

6. A method according to claim 5 in which the said malodor counteractant is introduced into the air together with a plurality of fragrance materials and the perceived total odour intensity in the air is reduced and the perceived malodor intensity is substantially eliminated.

7. A method according to claim 5 in which the said malodor counteractant is introduced into the air together with a plurality of fragrance materials, the total amount of fragrance materials being insufficient, in the absence of the malodor counteractant, to mask the malodor.

8. A method according to claim 8 in which $R^3$ is selected from the group consisting of hydrogen and $C_{1-3}$ alkyl, $R^1$ is methyl and $R^2$ is selected from the group consisting of hydrogen and methyl.

9. A method according to claim 5 in which X is —$COR^3$, $R^2$ is hydrogen, $R^1$ is methyl and $R^3$ is selected from the group consisting of $CH_3$ and $C_3H_7$.

10. The method of claim 5 wherein $R^3$ represents $C_{2-6}$ alkyl.

* * * * *